(12) United States Patent
Bright et al.

(10) Patent No.: US 6,525,196 B1
(45) Date of Patent: Feb. 25, 2003

(54) 5HT1 ANTAGONISTS FOR ANTIDEPRESSANT THERAPY

(75) Inventors: Gene M. Bright, Groton, CT (US); Kishor A. Desai, Ledyard, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/454,509

(22) Filed: Dec. 6, 1999

Related U.S. Application Data

(60) Provisional application No. 60/113,957, filed on Dec. 28, 1998.

(51) Int. Cl.⁷ .................. A61K 31/495; A61K 31/423; C07D 213/00; C07D 261/00; C07D 403/00
(52) U.S. Cl. ................... 544/295; 544/359; 546/1; 548/246; 514/252.13; 514/252.14; 514/253.11; 514/379
(58) Field of Search ............... 514/253.11, 252.14, 514/252.13, 379; 544/295, 359; 548/246; 546/1

(56) References Cited

FOREIGN PATENT DOCUMENTS

| WO | 9215580 | * | 9/1992 |
| WO | 9532967 | | 12/1995 |
| WO | 9850358 | | 11/1998 |
| WO | 9952907 | | 10/1999 |
| WO | 9906384 | | 11/1999 |

* cited by examiner

Primary Examiner—Richard L. Raymond
Assistant Examiner—Sudhaker B Patel
(74) Attorney, Agent, or Firm—P. C. Richardson; P. H. Ginsburg; A. D. Joran

(57) ABSTRACT

The present invention relates to compounds of formula 1,

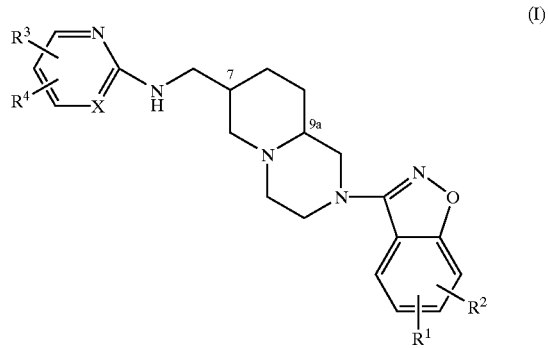

wherein $R^1$, $R^2$, $R^3$ and $R^4$ are defined as in the specification. These compounds are useful as psychotherapeutic agents.

20 Claims, No Drawings

5HT1 ANTAGONISTS FOR ANTIDEPRESSANT THERAPY

This application claims priority under 35 U.S.C. §119(e) from U.S. application Ser. No. 60/113,957 filed Dec. 28, 1998, which application is hereby incorporated by reference.

BACKGROUND OF THE INVENTION

The present invention relates to novel heteroaryl-aminoethyl/benzisoxazole substituted azabicyclic compounds, to intermediates for their preparation, to pharmaceutical compositions containing them and to their medicinal use. The compounds of the present invention include selective agonists and antagonists of serotonin 1 (5-HT1) receptors, specifically, of one or both of the 5-HT1A and 5-HT1D receptors. They are useful in treating or preventing migraine, depression and other disorders for which a 5-HT1 agonist or antagonist is indicated.

European Patent Publication 434,561, published on Jun. 26, 1991, refers to 7-alkyl, alkoxy, and hydroxy substituted-1-(4-substituted-1-piperazinyl)-naphthalenes. The compounds are referred to as 5-HT1 agonists and antagonists useful for the treatment of migraine, depression, anxiety, schizophrenia, stress and pain.

European Patent Publication 343,050, published on Nov. 23, 1989, refers to 7unsubstituted, halogenated, and methoxy substituted-1-(4-substituted-1-piperazinyl)-naphthalenes as useful 5-HT1Aligand therapeutics.

PCT publication WO 94/21619, published Sep. 29, 1994, refers to naphthalene derivatives as 5-HT1 agonists and antagonists.

PCT publication WO 96/00720, published Jan. 11, 1996, refers to naphthyl ethers as useful 5-HT1 agonists and antagonists.

European Patent Publication 701,819, published Mar. 20, 1996, refers to the use of 5-HT1 agonists and antagonists in combination with a 5-HT re-uptake inhibitor.

Glennon et al., refers to 7-methoxy-1-(1-piperazinyl)-naphthalene as a useful 5-HT1 ligand in their article "5-HT1D Serotonin Receptors", *Clinical Drug Res. Dev.*, 22, 25–36 (1991).

Glennon's article "Serotonin Receptors: Clinical Implications", *Neuroscience and Behavioral Reviews*, 14, 35–47 (1990), refers to the pharmacological effects associated with serotonin receptors including appetite suppression, thermoregulation, cardiovascular/hypotensive effects, sleep, psychosis, anxiety, depression, nausea, emesis, Alzheimer's disease, Parkinson's disease and Huntington's disease.

World Patent Application WO 95/31988, published Nov. 30, 1995, refers to the use of a 5-HT1D antagonist in combination with a 5-HT1A antagonist to treat CNS disorders such as depression, generalized anxiety, panic disorder, agoraphobia, social phobias, obsessive-compulsive disorder, post-traumatic stress disorder, memory disorders, anorexia nervosa and bulimia nervosa, Parkinson's disease, tardive dyskinesia, endocrine disorders such as hyperprolactinemia, vasospasm (particularly in the cerebral vasculature) and hypertension, disorders of the gastrointestinal tract where changes in motility and secretion are involved, as well as sexual dysfunction.

G. Maura et al., *J. Neurochem*, 66 (1), 203–209 (1996), have stated that administration of agonists selective for 5-HT1A receptors or for both 5-HT1A and 5-HT1D receptors might represent a great improvement in the treatment of human cerebellar ataxias, a multifaceted syndrome for which no established therapy is available.

European Patent Publication 666,261, published Aug. 9, 1995 refers to thiazine and thiomorpholine derivatives which are claimed to be useful for the treatment of cataracts.

SUMMARY OF THE INVENTION

The present invention relates to compounds of the formula

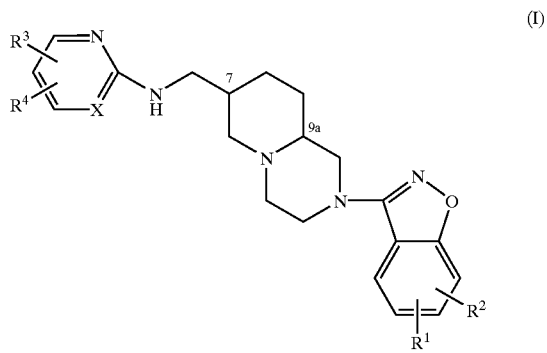

(I)

wherein $R^1$, $R^2$, $R^3$ and $R^4$ are selected, independently, from hydrogen, halo (e.g., chloro, fluoro, bromo or iodo), ($C_1$–$C_4$) alkyl optionally substituted with from one to three fluorine atoms, ($C_1$–$C_4$)alkoxy optionally substituted with from one to three fluorine atoms, and ($C_1$–$C_4$)alkoxy-($C_1$–$C_4$)alkyl wherein each of the alkyl moieties may optionally be substituted with from one to three fluorine atoms; and X is CH or N;

and the pharmaceutically acceptable salts thereof.

Examples of preferred compounds of the formula I are those having the absolute stereochemical configuration defined as 7R, 9aS-trans or as 7S, 9aS-cis.

Other preferred compounds of the formula I are those wherein $R^3$ and $R^4$ selected, independently, from hydrogen, fluoro, chloro and methyl.

Examples of specific compounds of this invention are the following compounds of their pharmaceutically acceptable salts:

(7R,9aS)-trans-(2-Benzo[d]isoxazol-3-yl-octahydro-pyrido[1,2-a]pyrazin-7-ylmethyl)-(5-methyl-pyrimidin-2-yl)-amine;

(7S,9aS)-cis-(2-Benzo[d]isoxazol-3-yl-octahydro-pyrido[1,2-a]pyrazin-7-ylmethyl)-(5-methyl-pyrimidin-2-yl)-amine;

(7R,9aS)-trans-(2-Benzo[d]isoxazol-3-yl-octahydro-pyrido[1,2-a]pyrazin-7-ylmethyl)-(5-chloro-pyrimidin-2-yl)-amine;

(7S,9aS)-cis-(2-Benzo[d]isoxazol-3-yl-octahydro-pyrido[1,2-a]pyrazin-7-ylmethyl)-(5-chloro-pyrimidin-2-yl)-amine;

(7R,9aS)-trans-(5-Chloro-pyrimidin-2-yl)-[2-(5-fluoro-benzo[d]isoxazol-3-yl)-octahydro-pyrido[1,2-a]pyrazin-7-ylmethyl]-amine;

(7S,9aS)-cis-(5-Chloro-pyrimidin-2-yl)-[2-(5-fluoro-benzo[d]isoxazol-3-yl)-octahydro-pyrido[1,2-a]pyrazin-7-ylmethyl]-amine;

(7R,9aS)-trans-[2-(5-Fluoro-benzo[d]isoxazol-3-yl)-octahydro-pyrido[1,2-a]pyrazin-7-ylmethyl]-(5-methyl-pyrimidin-2-yl)-amine;

(7S,9aS)-cis-[2-(5-Fluoro-benzo[d]isoxazol-3-yl)-octahydro-pyrido[1,2-a]pyrazin-7-ylmethyl]-(5-methyl-pyrimidin-2-yl)-amine;

(7R,9aS)-trans-(2-Benzo[d]isoxazol-3-yl-octahydro-pyrido[1,2-a]pyrazin-7-ylmethyl)-(5-fluoro-pyridin-2-yl)-amine;

(7S,9aS)-cis-(2-Benzo[d]isoxazol-3-yl-octahydro-pyrido[1,2-a]pyrazin-7-ylmethyl)-(5-fluoro-pyridin-2-yl)-amine;

(7R,9aS)-trans-[2-(5-Fluoro-benzo[d]isoxazol-3-yl)-octahydro-pyrido[1,2-a]pyrazin-7-ylmethyl]-(5-fluoro-pyridin-2-yl)-amine;

(7S,9aS )-cis-[2-(5-Fluoro-benzo[d]isoxazol-3-yl)-octahydro-pyrido[1,2-a]pyrazin-7-ylmethyl]-(5-fluoro-pyridin-2-yl)-amine;

(7R,9aS)-trans-(2-Benzo[d]isoxazol-3-yl-octahydro-pyrido[1,2-a]pyrazin-7-ylmethyl)-(5-fluoro-3-methyl-pyridin-2-yl)-amine;

(7S,9aS )-cis-(2-Benzo[d]isoxazol-3-yl-octahydro-pyrido[1,2-a]pyrazin-7-ylmethyl)-(5-fluoro-3-methyl-pyridin-2-yl)-amine;

(7R,9aS)-trans-[2-(5-Fluoro-benzo[d]isoxazol-3-yl)-octahydro-pyrido[1,2-a]pyrazin-7-ylmethyl]-(5-fluoro-3-methyl-pyridin-2-yl)-amine;

(7S,9aS)-cis-[2-(5-Fluoro-benzo[d]isoxazol-3-yl )-octahydro-pyrido[1,2-a]pyrazin-7-ylmethyl]-(5-fluoro-3-methyl-pyridin-2-yl)-amine, and (7R,9aS)-trans-(2-Benzo[d]isoxazol-3yl-octahydro-pyrido[1,2-a]pyrazin-7-yl-methyl)-(5-fluoro-pyrimidin-2-yl)-amine.

The present invention also relates to a pharmaceutical composition for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders) in a mammal, preferably a human, comprising an amount of a compound of the formula I or a pharmaceutically acceptable salt thereof effective in treating such disorder or condition and a pharmaceutically acceptable carrier.

The present invention also relates to a pharmaceutical composition for treating a disorder or condition that can be treated by modulating serotonergic neurotransmission in a mammal, preferably a human, comprising an amount of a compound of the formula I, or a pharmaceutically acceptable salt thereof, effective in treating such disorder or condition and a pharmaceutically acceptable carrier. Examples of such disorders and conditions are those enumerated in the preceding paragraph.

The present invention also relates to a method for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer, (e.g., small cell lung carcinoma), chronic paroxysmal hemicrania and headache (associated with vascular disorders) in a mammal, preferably a human, comprising administering to a mammal in need of such treatment an amount of a compound of the formula I, or a pharmaceutically acceptable salt thereof, that is effective in treating such disorder or condition.

The present invention also relates to a method for treating a disorder or condition that can be treated by modulating serotonergic neurotransmission in a mammal, preferably a human, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders) in a mammal, preferably a human, comprising a serotonin 1A receptor antagonizing or agonizing effective amount, or a serotonin 1D receptor antagonizing effective amount, of a compound of the formula I, or a pharmaceutically acceptable salt thereof, and a pharmaceutically acceptable carrier.

The present invention also relates to a pharmaceutical composition for treating a disorder or condition that can be treated by modulating serotonergic neurotransmission in a mammal, preferably a human, comprising a serotonin 1A receptor antagonizing or agonizing effective amount, or a serotonin 1D receptor antagonizing effective amount, of a compound of the formula I, or a pharmaceutically acceptable salt thereof, and a pharmaceutically acceptable carrier.

The present invention also relates to a method for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders) in a mammal, preferably a human, comprising administering to a mammal requiring such treatment a serotoninn 1A receptor antagonizing or agonizing effective amount, or a serotonin 1D receptor antagonizing effective amount, of a compound of the formula I or a pharmaceutically acceptable salt thereof.

The present invention also relates to a method for treating a disorder or condition that can be treated by modulating serotonergic neurotransmission in a mammal, preferably a human, comprising administering to a mammal requiring such treatment a serotonin 1A receptor antagonizing or agonizing effective amount, or a serotonin 1D receptor antagonizing effective amount, of a compound of the formula I or a pharmaceutically acceptable salt thereof.

The present invention relates to a pharmaceutical composition for treating a condition or disorder that can be treated by modulating serotonergic neurotransmission in a mammal, preferably a human, comprising:

a) a pharmaceutically acceptable carrier;
b) a compound of the formula I or a pharmaceutically acceptable salt thereof; and
c) a 5-HT re-uptake inhibitor, preferably sertraline, or a pharmaceutically acceptable salt thereof;

wherein the amount of the active compounds (i.e., the compound of formula I and the 5-HT re-uptake inhibitor) are such that the combination is effective in treating such disorder or condition.

The present invention also relates to a method for treating a disorder or condition that can be treated by modulating serotonergic neurotransmission in a mammal, preferably a human, comprising administering to a mammal requiring such treatment:

a) a compound of the formula I, defined above, or a pharmaceutically acceptable salt thereof; and
b) a 5-HT re-uptake inhibitor, preferably sertraline, or a pharmaceutically acceptable salt thereof;

wherein the amounts of the active compounds (i.e., the compound of formula I and the 5-HT re-uptake inhibitor) are such that the combination is effective in treating such disorder or condition.

The present invention also relates to a method for treating a disorder or condition that can be treated by modulating serotonergic neurotransmission in a mammal, preferably a human, comprising administering to said mammal requiring such treatment:

a) a 5-HT1A agonist or antagonist or a pharmaceutically acceptable salt thereof; and
b) a 5-HT1D antagonist of formula I or a pharmaceutically acceptable salt thereof;

wherein the amounts of each active compound (i.e., the 5-HT1A agonist or antagonist and the 5-HT1D antagonist) are such that the combination is effective in treating such disorder or condition.

The, present invention also relates to a pharmaceutical composition for treating a disorder or condition that can be treated by modulating serotonergic neurotransmission in a mammal, preferably a human, comprising:

a) a 5-HT1A agonist or antagonist or a pharmaceutically acceptable salt thereof; and
b) a 5-HT1D antagonist of formula I or a pharmaceutically acceptable salt thereof, wherein the amounts of each active compound (i.e., the 5-HT1A agonist or antagonist and the 5-HT1D antagonist) are such that the combination is effective in treating such disorder or condition.

This invention also relates to the pharmaceutically acceptable acid addition salts of the compounds of formula I. Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malate, di-p-toluoyl tartaric acid, and mandelic acid.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. The invention includes all enantiomers, diastereomers, and other stereoisomers of such compounds of formula I, as well as racemic and other mixtures thereof.

The present invention also relates to all radiolabelled forms of the compounds of the formula I. Preferred radiolabelled compounds of formula I are those wherein the radiolabels are selected from as $^3H$, $^{11}C$, $^{14}C$, $^{18}F$, $^{123}I$ and $^{125}I$. Such radiolabelled compounds are useful as research and diagnostic tools in metabolism pharmacokinetics studies and in binding assays in both animals and man.

"Modulating serotonergic neurotransmission," as used herein, refers to increasing or improving, or decreasing or retarding the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenobarbitol, and benzodiazepines (e.g., Valium (trademark)). "Treating a chemical dependency," as used herein, means reducing or alleviating such dependency.

Sertraline, (1S-cis)-4-(3,4-dichlorophenyl)-1,2,3,4-tetrahydro-N-methyl-1-naphthalenamine, as used herein has the chemical formula $C_{17}H_{17}NCl_2$ and the following structural formula

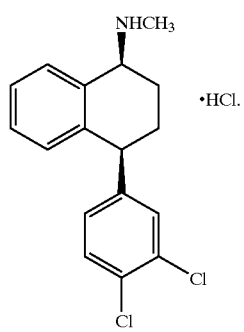

Its synthesis is described in U.S. Pat. No. 4,536,518, assigned to Pfizer Inc. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation.

DETAILED DESCRIPTION OF THE INVENTION

Compounds of the formula I may be prepared according to the following reaction schemes and discussion. Unless otherwise indicated, Het, $R^1$, and $R^2$, $R^3$ and $R^4$, and structural formula I in the reaction schemes and discussion that follow are as defined above.

SCHEME 1

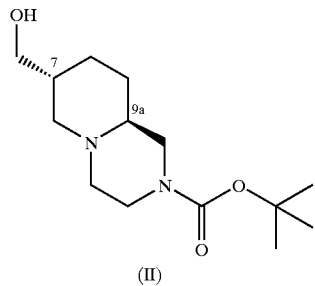 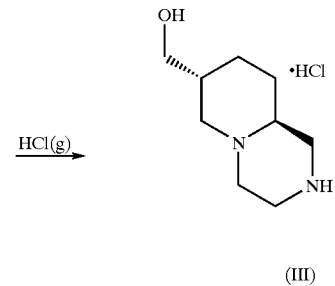

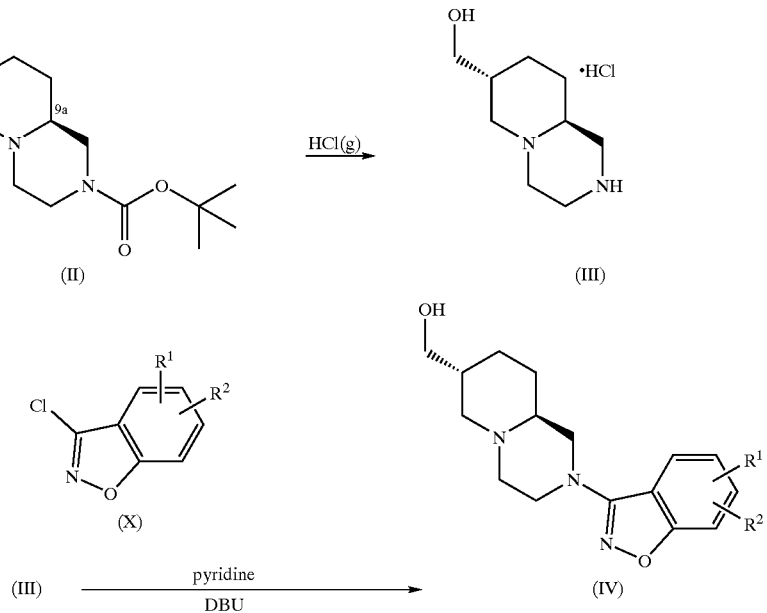

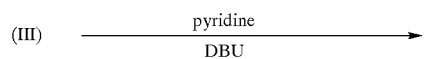

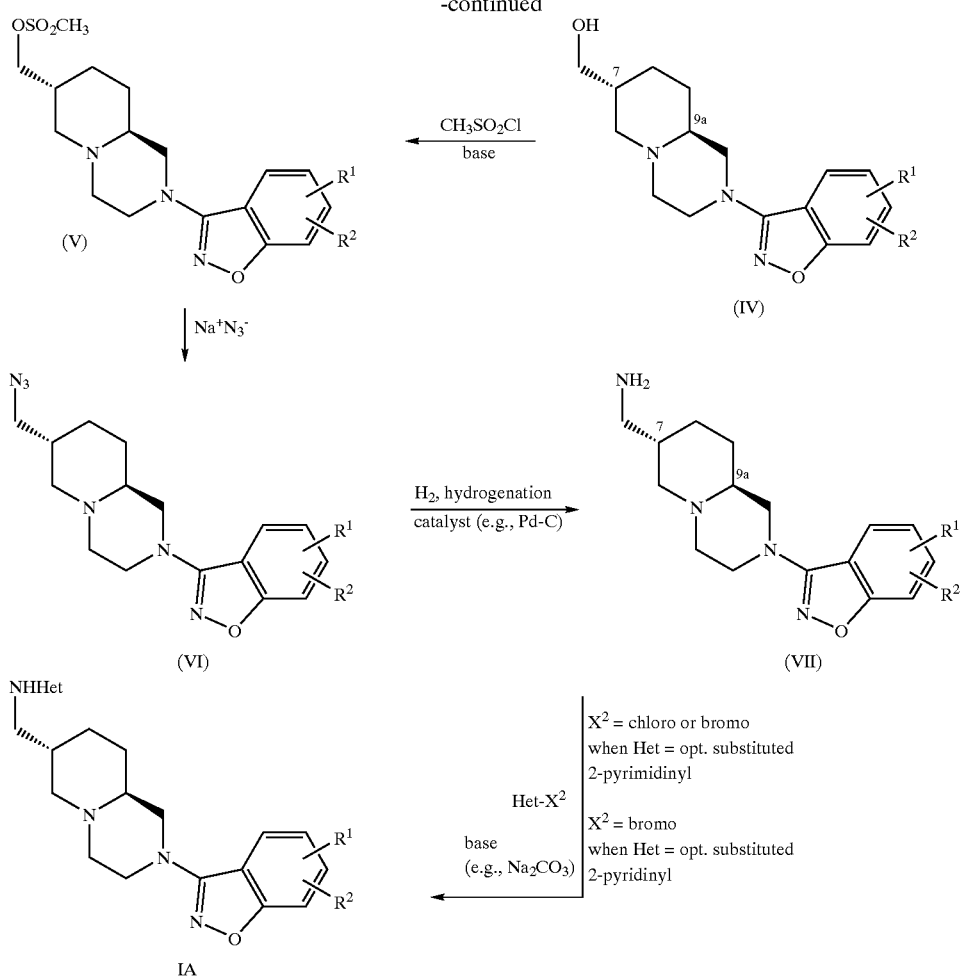

Scheme 1 illustrates a method of preparing compounds of the formula I having (7R, 9aS)-trans, (7S, 9aS)-cis or racemic stereochemistry. These are referred to in Scheme 1 as compounds of the formula IA. The same procedure can be used to produce all compounds of the formula I, regardless of their stereochemistry, by using a starting material of the formula II having the same stereochemistry at the 7 and 9a chiral centers as the desired product. Referring to Scheme 1, the compound formula II is deprotected to form the hydrochloric acid addition salt of formula III. This can be accomplished using anhydrous hydrochloric acid (HCl) in diethyl ether, another dialkyl ether or a halocarbon solvent at about room temperature. This reaction can also be carried out without a solvent using trifluoroacetic acid, in which case the trifluoroacetic acid addition salt is formed. This reaction is generally run from about 2 to about 18 hours.

The corresponding compound of formula IV can be formed by reacting the compound of formula III from the foregoing reaction with the appropriate compound of formula X, wherein $R^1$ and $R^2$ are as defined above in the definition of compounds of the formula I, and 1,8-diazabicyclo[5.4.0]-undec-7-ene (DBU). This reaction is typically conducted in pyridine, at a temperature from about 50° C. to about 110° C., for a period of about 1 to about 48 hours.

The compound of formula IV can then be converted into the compound of formula V by reacting it with methane-sulfonyl chloride in the presence of a tertiary amine base such as triethylamine (TEA), in methylene chloride or another halocarbon solvent, at a temperature from about −5° C. to about room temperature, for a period of about 10 minutes to about 2 hours.

Reaction of the compound of formula V with a compound of the formula $Na^+N_3^-$, or, more generally, $M^+N_3^-$, wherein $M^+$ is a suitable alkali metal cation such as $Li^+$ or $K^+$, or $M^+$ is a tetra-$(C_1–C_4)$alkylammonium cation such as tetrabutylammonium, yields the corresponding compound of formula VI. Hydrogenation of the resulting compound of formula VI using hydrogen gas at a pressure of from about 1–5 atmospheres, in the presence of a catalyst such as palladium on carbon (Pd—C), in a solvent such as ethanol or methanol, at a temperature from about 0° C. to about 60° C., preferably at about 20° C., yields the corresponding amine of formula VII.

The compound of formula VII can be converted into the final product of formula IA by reacting it with a compound of the formula Het—$X^2$, wherein Het is

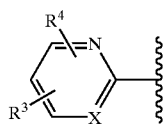

and $X^2$ is chloro or bromo when Het is optionally substituted 2-pyrimidinyl and X is bromo when Het is optionally substituted 2-pyridinyl. This reaction is typically carried out in a high boiling solvent such as N,N-dimethylformamide (DMF) or iso-amylalcohol in presence of a base such as sodium carbonate ($Na_2CO_3$) or potassium carbonate ($K_2CO_3$), preferably sodium carbonate, at a temperature from about 80° C. to about the reflux temperature of the solvent, preferably at about 100° C.

Unless indicated otherwise, the pressure of each of the above reactions is not critical. Generally, the reactions will be conducted at a pressure of about one to about three atmospheres, preferably at ambient pressure (about one atmosphere).

The compounds of the formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)]salts.

Compounds of the formula I and their pharmaceutically acceptable salts (hereinafter also referred to, collectively, as "the active compounds") are useful psychotherapeutics and are potent agonists and/or antagonists of the serotonin 1A (5-HT1A) and/or serotonin 1D (5-HT1D) receptors. The active compounds are useful in the treatment of hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e,g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders).

The affinities of the compounds of this invention for the various serotonin-1 receptors can be determined using standard radioligand binding assays as described in the literature. The 5-HT1A affinity can be measured using the procedure of Hoyer et al. (*Brain Res.,* 376, 85 (1986)). The 5-HT1D affinity can be measured using the procedure of Heuring and Peroutka (*J. Neurosci.,* 7, 894 (1987)).

The in vitro activity of the compounds of the present invention at the 5-HT1D binding site may be determined according to the following procedure. Bovine caudate tissue is homogenized and suspended in 20 volumes of a buffer containing 50 mM TRIS.hydrochloride (tris [hydroxymethyl]aminomethane hydrochloride) at a pH of 7.7. The homogenate is then centrifuged at 45,000 G for 10 minutes. The supernatant is then discarded and the resulting pellet resuspended in approximately 20 volumes of 50 mM TRIS.hydrochloride buffer at pH 7.7. This suspension is then pre-incubated for 15 minutes at 37° C., after which the suspension is centrifuged again at 45,000 G for 10 minutes and the supematant discarded. The resulting pellet (approximately 1 gram) is resuspended in 150 ml of a buffer of 15 mM TRIS.hydrochloride containing 0.01 percent ascorbic acid with a final pH of 7.7 and also containing 10 mM pargyline and 4 mM calcium chloride ($CaCl_2$). The suspension is kept on ice at least 30 minutes prior to use.

The inhibitor, control or vehicle is then incubated according to the following procedure. To 50 ml of a 20 percent dimethylsulfoxide (DMSO)/80 percent distilled water solution is added 200 ml of tritiated 5-hydroxytryptamine (2 nM) in a buffer of 50 mM TRIS.hydrochloride containing 0.01 percent ascorbic acid at pH 7.7 and also containing 10 mM pargyline and 4 mM calcium chloride, plus 100 nM of 8-hydroxy-DPAT (dipropylaminotetraline) and 100 nM of mesulergine. To this mixture is added 750 ml of bovine caudate tissue, and the resulting suspension is vortexed to ensure a homogenous suspensions. The suspension is then incubated in a shaking water bath for 30 minutes at 25° C. After incubation is complete, the. suspension is filtered using glass fiber filters (e.g., Whatman GF/B-filters). The pellet is then washed three times with 4 ml of a buffer of 50 mM TRIS.hydrochloride at pH 7.7. The pellet is then placed in a scintillation vial with 5 ml of scintillation fluid (aquasol 2) and allowed to sit overnight. The percent inhibition can be calculated for each dose of the compound. An $IC_{50}$ value can then be calculated from the percent inhibition values.

The activity of the compounds of the present invention for 5-HT1A binding ability can be determined according to the following procedure. Rat brain cortex tissue is homogenized and divided into samples of 1 gram lots and diluted with 10 volumes of 0.32 M sucrose solution. The suspension is then centrifuged at 900 G for 10 minutes and the supernate separated and recentrifuged at 70,000 G for 15 minutes. The supernate is discarded and the pellet re-suspended in 10 volumes of 15 mM TRIS.hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS.hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 mm pargyline and kept on ice.

The tissue is then incubated according to the following procedure. Fifty microliters of control, inhibitor, or vehicle (1 percent DMSO final concentration) is prepared at various dosages. To this solution is added 200 ml of tritiated DPAT at a concentration of 1.5 nM in a buffer of 50 mM TRIS.hydrochloride at pH 7.7 containing 4 mM calcium chloride, 0.01 percent ascorbic acid and pargyline. To this solution is then added 750 ml of tissue and the resulting suspension is vortexed to ensure homogeneity. The suspension is then incubated in a shaking water bath for 30 minutes at 37° C. The solution is then filtered, washed twice with 4 ml of 10 mM TRIS.hydrochloride at pH 7.5 containing 154 mM of sodium chloride. The percent inhibition is calculated for each dose of the compound, control or vehicle. $IC_{50}$ values are caiculated from the percent inhibition values.

The compounds of formula I of the present invention described in the following Examples were assayed for 5-HT1A and 5-HT1D affinity using the aforementioned procedures. All such compounds of the invention that were tested exhibited $IC_{50}$'s less than 0.60 mM for 5-HT1D affinity and $IC_{50}$'s less than 1.0 mM for 5-HTIA affinity.

The agonist and antagonist activities of the compounds of the invention at 5-HT1A and 5-HT1D receptors can be determined using a single saturating concentration according to the following procedure. Male Hartley guinea pigs are decapitated and 5-HT1A receptors are dissected out of the hippocampus, while 5-HT1D receptors are obtained by slicing at 350 mM on a McIlwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 mM GTP and 0.5–1 microcuries of [32P]-ATP (30 Ci/mmol: NEG-003—New England Nuclear). Incubation is initiated by the addition of tissue to siliconized microfuge tubes (in triplicate) at 30° C. for 15 minutes. Each tube receives 20 mL tissue, 10 mL drug or buffer (at 10× final concentration), 10 mL 32 nM agonist or buffer (at 10× final concentration), 20 mL forskolin (3 mM final concentration) and 40 mL of the preceding reaction mix. Incubation is terminated by the addition of 100 mL 2% SDS, 1.3 mM cAMP, 45 mM ATP solution containing 40,000 dpm [$^3$H]AMP (30 Ci/mmol: NET-275—New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 mM (R)-8-OH-DPAT for 5-HT1A receptors, and 320 nM 5-HT for 5-HT1D receptors. Percent inhibitions by the test compounds are then calculated in relation to the inhibitory effect of (R)-8-OH-DPAT for 5-HT1A receptors or 5-HT for 5-HT1D receptors. The reversal of agonist induced inhibition of forskolin-stimulated adenylate cyclase activity is calculated in relation to the 32 nM agonist effect.

The compounds of the invention can be tested for in vivo activity for antagonism of 5-HT1D agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a 5-HT1D agonist, such as [3-(1-methylpyrrolidin-2-ylmethyl)-1H-indol-5-yl]-(3-nitropyridin-3-yl)-amine, which can be prepared as described in PCT publication WO93/111 06, published Jun. 10, 1993 which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-HT1D agonist is then administered at 0 minutes and temperatures are taken 30, 60, 120 and 240 minutes later.

In subcutaneous screening experiments, a pre-drug baseline temperature reading is made at −30 minutes. The test compound and 5HT1D agonists are given concurrently and temperatures are taken at 30, 60, 120 and 240 minutes later.

Data are analyzed with two-way analysis of variants with repeated measures in Newman-Keuls post hoc analysis.

The active compounds of the invention can be evaluated as anti-migraine agents by testing the extent to which they mimic sumatriptan in contracting the dog isolated saphenous vein strip [P. P. A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. Pharmacol.*, 96, 83 (1989).

The serotonin 5-HT1 agonist activity can be determined by the in vitro receptor binding assays, as described for the 5-HT1A receptor using rat cortex as the receptor source and [$^3$H]-8-OH-DPAT as the radioligand [D. Hoyer et al. *Eur. J. Pharm.*, 118, 13 (1985)] and as described for the 5-HT1D receptor using bovine caudate as the receptor source and [3H]serotonin as the radioligand [R. E. Heuring and S. J. Peroutka, *J. Neuroscience*, 7, 894 (1987)]. Of the active compounds tested, all exhibited an $IC_{50}$ in either assay of 1 mM or less.

The compounds of formula I may advantageously be used in conjunction with one or more other therapeutic agents, for instance, different antidepressant agents such as tricyclic antidepressants (e.g., amitriptyline, dothiepin, doxepin, trimipramine, butripyline, clomipramine, desipramine, imipramine, iprindole, lofepramine, nortriptyline or protriptyline), monoamine oxidase inhibitors (e.g., isocarboxazid, phenelzine or tranylcyclopramine) or 5-HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist e.g., bromocriptine, lysuride or pergolide). It is to be understood that the present invention covers the use of a compound of general formula (I) or a physiologically acceptable salt or solvate thereof in combination with one or more other therapeutic agents.

Compounds of the formula I and the pharmaceutically acceptable salts thereof, in combination with a 5-HT re-uptake inhibitor (e.g., fluvoxamine, sertraline, fluoxetine or paroxetine), preferably sertraline, or a pharmaceutically acceptable salt or polymorph thereof (the combination of a compound of formula I with a 5-HT re-uptake inhibitor is referred herein to as "the active combination"), are useful psychotherapeutics and may be used in the treatment or prevention of disorders the treatment or prevention of which is facilitated by modulating serotonergic neurotransmission such as hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g., small cell lung carcinoma), chronic paroxysmal hemicrania and headache (associated with vascular disorders).

Serotonin (5-HT) re-uptake inhibitors, preferably sertraline, exhibit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

U.S. Pat. No. 4,536,518 describes the synthesis, pharmaceutical composition and use of sertraline for depression and is hereby incorporated by reference in its entirety.

Activity of the active combination as antidepressants and related pharmacological properties can be determined by methods (1)–(4) below, which are described in Koe, B. et al., *Journal of Pharmacology and Experimental Therapeutics*, 226 (3), 686–700 (1983). Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., depression) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, iozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg to about 100 mg per kg of body weight per day of a 5-HT re-uptake inhibitor, preferably sertraline, preferably from about 0.1 mg to about 10 mg per kg of body weight per day of sertraline; with from about 0.001 mg. to about 100 mg per kg of body weight per day of a compound of formula I, preferably from about 0.01 mg to about 10 mg per kg of body weight per day of a compound of formula I, although variations will necessarily occur depending upon the conditions of the subject being treated and the particular route of administration chosen.

The following Examples illustrate the preparation of the compounds of the present invention. Melting points are uncorrected. NMR data are reported in parts per million and are referenced to the deuterium lock signal from the sample solvent (deuteribchloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 47–61 micron mesh silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

(7R,9aS)-TRANS-[2-(5-FLUORO-BENZO[d] ISOXAZOL-3-YL)-OCTAHYDRO-PYRIDO[1,2-a] PYRAZIN-7-YLMETHYL]-(5-FLUORO-PYRIMIDIN-2-YL)-AMINE

Step 1

(7R,9aS)-trans-7-Azidomethyl-2-(5-fluoro-benzo[d] isoxazol-3-yl)-octahydro-pyrido[1,2-a]pyrazin A mixture consisting of (7R,9aS)-trans-methane sulfonic acid 2-(5-fluoro-benzo[d]isoxazol-3-yl)-octahydro-pyrido [1,2-a]pyrazin-7-yl ester (3.74 g, 9.8 mmol) and sodium azide (1.27 g, 19.6 mmol) in N,N-dimethylformamide (20 ml) was stirred and heated at 75° C. for 18 hours. Water (150 ml) was added, and the resulting solution was then extracted with three 20 ml portions of methylene chloride. The combined organic extracts were, in turn, extracted with water (50 ml), dried (anhydrous sodium sulfate), and concentrated in vacuo to afford a tacky solid. Pulping with hexanes (50 ml) afforded a granular solid which was filtered. The filter cake was washed with hexanes (20 ml) and dried in vacuo to afford the title compound as a colorless amorphous solid (2.81 g, 87% yield). TLC $R_f$ (silica gel plates; elution with methanol/methylene chloride=4:96 in volume; UV detection): 0.48.

MS m/z 331 (M+1).

Step 2

(7R,9aS)-trans-[2-(5-Fluoro-benzo[d]isoxazol-3-yl)-octahydro-pyrido[1,2-a]pyrazin-7-yl]-methylamine The title compound from the previous step (2.81 g, 9.24 mmol), dissolved in an ethanol/methanol mixture (70 ml and 20 ml, respectively), was hydrogenated (40 psi; 700 mg of 5% palladium-on-carbon catalyst) for 2.5 hours. The catalyst was removed by filtration. Concentration of the filtrate in vacuo afforded the title compound (2.42 g, 94% yield) as a colorless amorphous solid.

MS m/z 305 (M+1).

Step 3

(7R,9aS)-trans-[2-(5-Fluoro-benzo[d]isoxazol-3-yl)octahydro-pyrido[1,2-a]pyrazin-7-yl]-methyl]-(5-fluoro-pyrimidin-2-yl)-amine To a partial solution of the title compound from the previous step (300 mg, 1.0 mmol) in N,N-dimethylformamide (3 ml), sodium carbonate (210 mg, 2.0 mmol) and 2-chloro-5-fluoro-pyrimidine [131 mg, 1.0 mmol; *Acta Chem. Scand.*, 39, 691–696 (1985); *J. Fluorine Chem.*, 45, 417430 (1989)] were added, and the well-stirred mixture was heated at 100° C. for 18 hours. Methylene chloride (20 ml) and water (50 ml) were added, and the heterogeneous mixture was vigorously stirred before extraction with a fresh 20 ml portion of methylene chloride. The separated organic extract was, in turn, extracted with water (30 ml), dried (anhydrous sodium sulfate), and concentrated in vacuo to afford a tacky solid (354 mg). Flash chromatography of the entire sample (silica gel, 47–61 micron mesh; elution with methanol/methylene chloride=3:97 in volume) afforded the title (free base) product as a colorless amorphous solid (201 mg, 51% yield).

MS m/z 401 (M+1).

Title Compound Mono-Hydrochloride Salt

The free base title compound (200 mg, 0.5 mmol) was dissolved in methylene chloride (3 ml). A solution of anhydrous hydrogen chloride in diethyl ether (1.0 M; 600 µl; 0.6 mmol) was added, and the resulting solution was well stirred. Solvent removal in vacuo yielded the monohydrochloride salt of the title compound as an amorphous solid (179 mg, 82% yield).

Mono-hydrochloride $^{13}C$ NMR (125 MHz, CD$_3$OD) δ161.1, 160.6 (2), 160.0, 158.1, 156.4, 152.2, 150.3, 146.0, 119.0, 118.8, 116.1, 116.0, 111.6, 111.5, 107.5, 107.3, 61.9, 57.1, 52.9, 51.0, 45.8, 44.5, 34.9, 26.3, 26.0 ppm.

EXAMPLE 2

(7R,9aS)-TRANS-[2-(5-FLUORO-BENZO[d]ISOXAZOL-3-YL)-OCTAHYDRO-PYRIDO[1,2-a]PYRAZIN-7-YLMETHYL]-PYRIMIDIN-2-YL)-AMINE

To a partial solution of the title compound of Step 2, Example 1 (300 mg, 1.0 mmol) in N,N-dimethylformamide (3 ml), sodium carbonate (210 mg, 2.0 mmol) and 2-chloropyrimidine (113 mg, 2.0 mmol) were added, and the well-stirred mixture was heated at 120° C. for 18 hours. Water (50 ml) was added, and the mixture was then extracted with three 20 ml portions of methylene chloride. The combined organic extracts were, in turn, extracted with an equal volume of water, dried (anhydrous sodium sulfate), and concentrated in vacuo, yielding a (480 mg) foam. Flash chromatography of the entire sample (silica gel; elution with methanol/methylene chloride=4:96 in volume) afforded the title compound (176 mg, 46% yield) as a colorless amorphous solid. TLC $R_f$ (silica gel plates; elution with methanol/methylene chloride=4:96 in volume; UV detection): 0.27.

MS m/z 383 (M+1).

Title Compound Mono-Hydrochloride Salt

By the method of the previous example, the title compound mono-hydrochloride salt was prepared as a colorless amorphous solid.

Mono-hydrochloride $^{13}C$ NMR (125 MHz, CD$_3$OD) δ161.1, 160.6 (2), 160.0, 158.1, 155.1, 119.0, 118.8, 116.1, 116.0, 111.6, 111.5, 110.5, 107.6, 107.4, 100.0, 61.9, 56.9, 53.0, 51.0, 45.8, 44.1, 34.6, 26.2, 26.0 ppm.

EXAMPLE 3

(7R,9aS)-TRANS-[2-(5-FLUORO-BENZO[d]ISOXAZOL-3-YL)-OCTAHYDRO-PYRIDO[1,2-a]PYRAZIN-7-YLMETHYL]-PYRIDIN-2-YL)-AMINE

To a partial solution of the title compound of Step 2, Example 1 (300 mg, 1.0 mmol) in N,N-dimethylformamide (3 ml), sodium carbonate (210 mg, 2.0 mmol) and 2-bromopyridine 94 µl, 2.0 mmol) were added, and the well-stirred mixture was heated at 100° C. for 18 hours. An additional portion of 2-bromopyridine (94 µl, 2.0 mmol) was added, and the mixture was heated at 120° C. for an additional 6 days. Water (40 ml) was added, and the mixture was then extracted with three 20 ml portions of methylene chloride. The combined organic extracts were, in turn, extracted with water (40 ml), dried (anhydrous sodium sulfate), and concentrated in vacuo, yielding an amber oil (690 mg). Flash chromatography of the entire sample (silica gel, 47–61 micron mesh; elution with methanol/methylene chloride=4:96 in volume) afforded the title compound (94 mg, 25% yield) as a colorless amorphous solid. TLC $R_f$ (silica gel plates; elution with methanol/methylene chloride=4:96 in volume; UV detection): 0.34.

MS m/z 382 (M+1).

Title Compound Mono-Hydrochloride Salt

By the method of the previous example, the title compound mono-hydrochloride salt was prepared as a colorless amorphous solid.

Mono-hydrochloride $^{13}C$ NMR (125 MHz, CD$_3$OD) δ161.1, 160.6, 160.0, 158.1, 153.4, 144.0, 135.5, 119.0, 118.8, 116.1, 116.0, 114.0, 113.1, 111.6, 111.5, 107.5, 107.3, 61.9, 56.5, 53.0, 51.0, 45.8, 44.6, 34.0, 26.1, 26.0 ppm.

EXAMPLE 4

(7S,9aS)-CIS-[2-(5-FLUORO-BENZO[d]ISOXAZOL-3-YL-OCTAHYDRO-PYRIDO[1,2-a]PYRAZIN-7-YLMETHYL-(5-FLUORO-PYRIMIDIN-2-YL)-AMINE

Step 1

(7S,9aS)-cis-methane sulfonic acid 2-(5-fluoro-benzo[d]isoxazol-3-yl)-octahydro-pyrido[1,2-a]pyrazin-7-yl ester To an ice bath chilled solution of (7S,9aS)-cis-[2-(5-fluoro-benzo[d]isoxazol-3-yl)-octahydro-pyrido[1,2-a]pyrazin-7-yl]-methanol (3.0 g, 9.8 mmol) and triethylamine (1.71 ml, 12.0 mmol) in methylene chloride (40 ml), methane sulfonyl chloride (836 μl, 11.0 mmol) was added. The reaction was stirred for 20 minutes prior to quenching with 10% aqueous sodium bicarbonate (60 ml). The reaction mixture was then extracted with three 30 ml portions of methylene chloride. The combined organic extracts were, in turn, extracted with an equal volume of water, dried (anhydrous sodium sulfate), and concentrated in vacuo, yielding the title compound (3.73 g, 99% yield) as a yellow gum. TLC $R_f$ (silica gel plates; elution with methylene chloride/methanol=95:5 in volume; UV detection): 0.52.

MS m/z 384 (M+1).

Step 2

(7S,9aS)-cis-7-Azidomethyl-2-(5-fluoro-benzo[d]isoxazol-3-yl)-octahydro-pyrido[1,2-a]pyra A reaction mixture consisting of (7S,9aS)-cis-methane sulfonic acid 2-(5-fluoro-benzo[d]isoxazol-3-yl)-octahydro-pyrido[1,2-a]pyrazin-7-yl ester (3.73 g, 9.7 mmol) and sodium azide (1.23 g, 19.0 mmol) in N,N-dimethylformamide (20 ml) was stirred and heated at 75° C. for 18 hours. Water (50 ml) was added, and the resulting solution was extracted with three 50 ml portions of methylene chloride. The combined organic extracts were, in turn, extracted with water (50 ml), dried (anhydrous sodium sulfate), and concentrated in vacuo, yielding an amber oil (3.65 g). Flash chromatography of the entire sample (silica gel, 7–61 micron mesh; elution with methylene chloride/methanol=99:1 in volume) afforded the title compound (614 mg, 19% yield) as a colorless amorphous solid. TLC $R_f$ (silica gel plates; elution with methylene chloride/methanol=95:5 in volume; UV detection): 0.54.

MS m/z 331 (M+1).

Step 3

(7S,9aS)-cis-[2-(5-fluoro-benzo[d]isoxazol-3-yl)-octahydro-pyrido[1,2-a]pyrazin-7-yl]-methylamine The title compound from the previous step (614 mg, 1.86 mmol), dissolved in a methanol/ethanol solution (10 ml and 20 ml respectively) was hydrogenated (40 psi; 154 mg of 5% palladium-on-carbon catalyst) for 2 hours. The catalyst was filtered, and the filtrate was concentrated in vacuo, yielding the title compound (421 mg, 74% yield) as a colorless gum. TLC $R_f$ (silica gel plates; elution with methylene chloride/methanol=8:2 in volume; UV detection): 0.38.

MS m/z 305 (M+1).

Step 4

(7S,9aS)-cis-[2-(5-fluoro-benzo[d]isoxazol-3-yl)-octahydro-pyrido[1,2-a]pyrazin-7-yl-methyl]-(5-fluoro-pyrimidin-2-yl)-amine To a solution of the title compound from the previous step (421 mg, 1.4 mmol) in N,N-dimethylformamide (3 ml), sodium carbonate (293 mg, 2.8 mmol) and 2-chloro-5-fluoro-pyrimidine (183 mg, 1.4 mmol) were added. The reaction mixture was heated at 100° C. for 18 hours. Water (35 ml) was added, and the resulting solution was extracted with three 30 ml portions of methylene chloride. The combined organic extracts were, in turn, extracted with water (30 ml), dried (anhydrous sodium sulfate), and concentrated in vacuo to yield (618 mg). Flash chromatography of the entire sample (silica gel, 47–61 micron mesh; elution with methanol/methylene chloride=2.5:97.5 in volume) afforded the title compound (71 mg, 13% yield) as a white amorphous solid. TLC $R_f$ (silica gel plates; elution with methanol/methylene chloride=2.5:97.5 in volume): 0.30.

MS m/z 401 (M+1).

Free base $^{13}$C NMR (125 MHz, CDCl$_3$) δ161.7, 160.9, 160.1, 159.5, 157.6, 153.4, 151.4, 146.0, 145.9, 118.6, 118.3, 116.9 (2), 111.8, 111.7, 107.9, 107.7, 60.8, 57.7, 54.7, 54.1, 48.7, 44.3, 33.3, 26.1, 25.4 ppm.

EXAMPLE 5

(7S,9aS)-CIS-(2-BENZO[d]ISOXAZOL-3-YL)-OCTAHYDRO-PYRIDO[1,2-a]PYRAZIN-7-YLMETHYL)-PYRIMIDIN-2-YL-AMINE

Step 1

(7S,9aS)-cis-Methanesulfonic acid 2-(2,3-dihydro-benzo[d]isoxazol-3-yl)-octahydro-pyrido[1,2-a]pyrazin-7-ylmethyl-ester To an ice bath chilled solution of (7S,9aS)-cis-3-yl-octahydro-pyrido[1,2-a]pyrazin-7-yl)-methanol (1.00 g, 3.5 mmol) and triethylamine (610 μl, 4.4 mmol) in methylene chloride (20 ml), methanesulfonyl chloride (296 μl, 3.8 mmol) was added. The reaction was stirred for 15 minutes prior to quenching with 10% aqueous sodium bicarbonate (40 ml). The reaction mixture was then extracted with methylene chloride (20 ml). The organic extract was, in turn, extracted with water (two 30 ml portions), dried (anhydrous sodium sulfate), and concentrated in vacuo, yielding the title compound (quantitative yield) as an amber oil.

MS m/z 366 (M+1).

Step 2

(7S,9aS)-cis-Azidomethyl-2-benzo[d]isoxazol-3-yl-octahydro-pyrido[1,2-a]pyrazin

A mixture consisting of the mesylate product of the previous step (1.28 g, 3.5 mmol) and sodium azide (455 mg, 7.0 mmol) in N,N-dimethylformamide (7.5 ml) was stirred and heated at 75° C. for 18 hours. Water (50 ml) was added, and the resulting solution was extracted with three 40 ml portions of methylene chloride. The combined organic extracts were, in turn, extracted with water (40 ml), dried (anhydrous sodium sulfate), and concentrated in vacuo, yielding an amorphous solid (1.35 g). Flash chromatography of the entire sample (silica gel, 47–61 micron mesh; elution with methylene chloride/methanol=95.5:0.5 in volume) afforded the title compound (680 mg, 62% yield) as a colorless oil. TLC $R_f$ (silica gel plates; elution with methanol/methylene chloride=1:99 in volume; UV detection): 0.55.

MS m/z 313 (M+1).

Step 3

(7S,9aS)-cis-(2-Benzo[d]isoxazol-3-yl)-octahydro-pyrido[1,2-a]pyrazin-7-yl)-methylamine The title compound from the previous step (680 mg, 2.18 mmol), dissolved in a methanol/ethanol solution (4.85 ml and 17 ml respectively), was hydrogenated (40 psi; 170 mg of 5% palladium-on-carbon catalyst) for 2 hours. The catalyst was removed by filtration. Concentration of the filtrate in vacuo afforded the title compound (410 mg, 66% yield) as a colorless amorphous solid.

MS m/z 287 (M+1).

Step 4

(7S,9aS)-cis-(2-Benzo[d]isoxazol-3-yl-octahydro-pyrido[1,2-a]pyrazin-7-ylmethyl)-pyrimidin-2-yl-amine To a solution of the title compound from the previous step (200 mg, 0.7 mmol) in N,N-dimethylformamide (2 ml), sodium carbonate (148 mg, 1.4 mmol) and 2-chloropyrimidine (80 mg, 0.7 mmol) were added. The well-stirred reaction mixture was then heated at 120° C. for 18 hours. Water (40 ml) was added, and the resulting solution was extracted with three 20 ml portions of methylene chloride. The combined organic extracts were, in turn, extracted with water (40 ml), dried (anhydrous sodium sulfate), and concentrated in vacuo to afford an oil (248 mg). FI Ash chromatography of the entire sample (silica gel, 47–61 micron mesh; elution with methylene chloride/methanol=97:3 in volume) afforded the title compound as a colorless amorphous solid (65 mg, 25% yield). TLC $R_f$ (silica gel plates; elution with methanol/methylene chloride=3:97 in volume; UV detection): 0.72.

MS m/z 365 (M+1).

Free Base $^{13}$C NMR (125 MHz, CDCl$_3$) δ164.4, 163.0, 161.6, 158.5, 129.9, 122.7, 122.6, 116.6, 110.9, 110.8, 60.9, 57.7, 54.7, 54.1, 48.7, 43.6, 33.4, 26.2, 25.4 ppm.

EXAMPLE 6

(7S,9aS)-CIS-(2-BENZO[d]ISOXAZOL-3-YL-OCTAHYDRO-PYRIDO[1,2-a]PYRAZIN-7-YLMETHYL)-(5-FLUORO-PYRIMIDIN-2-YL)-AMINE

To a solution of the title compound of Step 3, Example 5, (200 mg, 0.7 mmol) in N,N-dimethylformamide (2 ml), sodium carbonate (148 g, 1.4 mmol) and 2-chloro-5-fluoropyrimidine (93 mg, 0.7 mmol) were added. The well-stirred reaction mixture was then heated at 120° C. for 18 hours. Water (40 ml) was added, and the resulting solution was extracted with three 20 ml portions of methylene chloride. The combined organic extracts were, in turn, extracted with a 40 ml portion of water, dried (anhydrous sodium sulfate), and concentrated in vacuo to yield an oil. Flash chromatography of the entire sample (silica gel, 47–61 micron mesh; elution with methylene chloride/methanol=97.5:2.5 in volume) afforded the title compound as a colorless amorphous solid (56 mg, 21% yield). TLC $R_f$ (silica gel plates; elution with methanol/methylene chloride=2.5:97.5 in volume; UV detection): 0.74.

MS m/z 383 (M+1).

Free Base $^{13}$C NMR (125 MHz, CDCl$_3$) δ164.4, 161.6, 160.1, 153.4, 151.4, 146.0, 145.9, 143.4, 129.9, 122.7, 122.6, 116.6, 110.9, 60.9, 57.7, 54.7, 54.1, 48.8, 44.3, 33.3, 26.2, 25.4 ppm.

EXAMPLE 7

(7R,9aS)-TRANS(2-BENZO[d]ISOXAZOL-3-YL-OCTAHYDRO-PYRIDO[1,2-a]PYRAZIN-7-YLMETHYL)-5-FLUORO-PYRIMIDIN-2-YL)-AMINE

Step 1

(7R,9aS)-trans-2-Benzo[d]isoxazol-3-yl-7-methanesulfonylmethyl-octahydro-pyrido[1,2-a]pyrazine To an ice bath chilled, well-stirred solution of (7R,9aS)-trans-7-hydroxymethyl-2-(1,2-benzisoxazol-3-yl)-2,3,4,6,7,8,9,9a-octahydro-1H-pyrido[1,2-a]pyrazine (F. J. Urban, U.S. Pat. No. 5,719,286; issued Feb. 17, 1998; 3.22 g, 11 mmol) in methylene chloride (60 ml), triethylamine (1.91 ml, 14 mmol) and methanesulfonyl chloride (954 μl, 12 mmol) were. sequentially added. After 10 minutes, the ice bath was removed, and the reaction was allowed to warm up over a 15 minute period. TLC inspection (silica gel plates; elution with methylene chloride/methanol=95:5 in volume; uv detection) indicated complete reaction. The reaction was quenched by addition of 10% dilute aqueous sodium bicarbonate (75 ml). The reaction mixture was then extracted with three 50 ml portions of methylene chloride. Solvent removal in vacuo afforded the title compound as a viscous oil (quantitative yield), which was used in the next step without further purification.

Step 2

(7R,9aS)-trans-7-Azidomethyl-2-benzo[d]isoxazol-3-yl-octahydro-pyrido[1,2-a]pyrazine To a solution of the title compound from the previous step (4.02 g, 11 mmol) in N,N-dimethylformamide (25 ml), sodium azide (1.43 g, 22 mmol) was added, and the resulting reaction mixture was stirred and heated at 70° C. for 60 hours. Water (100 ml) was added, and the mixture was then extracted with three 70 ml portions of methylene chloride. The combined organic extracts were in turn, extracted with water. The separated organic extract was dried (anhydrous sodium sulfate), and concentrated in vacuo affording a tan solid (4.25 g). Flash chromatography of the entire sample (silica gel, 47–61 micron mesh; elution with methylene chloride/methanol=99.25:0.75 in volume) afforded the title compound (1.80 g, 52% yield) as a colorless amorphous solid.

MS m/z 313 (M+1).

Step 3

(7R,9aS)-trans-(2-Benzo[d]isoxazol-3-yl-octahydro-pyrido[1,2-a]pyrazin-7-yl)-methylamine An ethanol/methanol (50 ml and 15 ml, respectively) solution of the title compound from the previous step (1.80 g, 5.75 mmol) was hydrogenated at 40 psi, utilizing 5% palladium-on-carbon catalyst (450 mg) for 1.5 hours. The catalyst was filtered, and the filtrate was concentrated in vacuo to afford the title compound (quantitative yield) as a colorless amorphous solid.

MS m/z 287 (M+1).

Step 4

(7R,9aS)-trans-(2-Benzo[d]isoxazol-3-yl-octahydro-pyrido[1,2-a]pyrazin-7-yl-methyl-(5-fluoro-pyrimidin-2-yl)-amine To a solution of the title compound from the previous step (1.65 g, 5.7 mmol) in N,N-dimethylformamide (12 ml), sodium carbonate (1.22 g, 12 mmol) and 2-chloro-5-fluoropyrimidine (764 mg, 5.7 mmol) were added. The well-stirred reaction mixture was then heated at 110° C. for 18 hours. Water (75 ml) was added, and the resulting solution was extracted with three 50 ml of methylene chloride. The combined organic extracts were dried (anhydrous sodium sulfate), and concentrated in vacuo to an oil (2.8 g). Flash chromatography of the entire sample (silica gel, 47–61 micron mesh, elution with methylene chloride/methanol 97:3 in volume) afforded the title compound (663 mg, 30% yield) as an amorphous colorless solid. TLC $R_f$ (silica gel plates; elution with methylene chloride/methanol=97:3 in volume; UV detection): 0.30.

MS m/z 383 (M+1).

Free Base $^{13}$C NMR (125 MHz, CDCl$_3$) δ164.2, 161.2, 159.7, 153.5, 151.0, 145.8, 145.6, 129.8, 122.5, 122.3, 116.3, 110.7, 60.4, 59.7, 54.4, 53.8, 48.4, 46.2, 36.6, 29.2, 28.4 ppm.

What is claimed is:
1. A compound of the formula

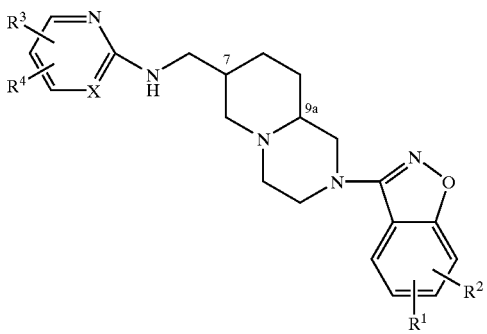

wherein $R^1$, $R^2$, $R^3$ and $R^4$ are selected, independently, from hydrogen, halo, ($C_1$–$C_4$) alkyl wherein said ($C_1$–$C_4$) alkyl is unsubstituted or substituted with from one to three fluorine atoms, ($C_1$–$C_4$)alkoxy wherein said ($C_1$–$C_4$)alkoxy is unsubstituted or substituted with from one to three fluorine atoms, and ($C_1$–$C_4$)alkoxy-($C_1$–$C_4$)alkyl wherein each of the alkyl moieties of said alkoxy ($C_1$–$C_4$ alkyl) is unsubstituted or substituted with from one to three fluorine atoms; and X is CH or N;

or a pharmaceutically acceptable salt thereof.

2. A compound according to claim 1, wherein having an absolute sterochemistry of (7R,9aS)-trans or (7S,9aS)-cis.

3. A compound according to claim 1 that is selected from:
(7R,9aS)-trans-[2-(5-Fluoro-benzo[d]isoxazol-3-yl)-octahydro-pyrido[1,2-a]pyrazin-7-ylmethyl]-(5-fluoro-pyrimidin-2-yl)-amine;
(7R,9aS)-trans-[2-(5-Fluoro-benzo[d]isoxazol-3-yl)-octahydro-pyrido[1,2-a]pyrazin-7-ylmethyl]-pyrimidin-2-yl)-amine;
(7S,9aS)-cis-[2-(5-Fluoro-benzo[d]isoxazol-3-yl-octahydro-pyrido[1,2-a]pyrazin-7-ylmethyl-(5-fluoro-pyridin-2-yl)-amine;
(7S,9aS)-cis-(2-Benzo[d]isoxazol-3-yl)-octahydro-pyrido[1,2-a]pyrazin-7-ylmethyl)-pyrimidin-2-yl-amine;
(7S,9aS)-cis-(2-Benzo[d]isoxazol-3-yl-octahydro-pyrido[1,2-a]pyrazin-7-ylmethyl)-(5-fluoro-pyrimidin-2-yl)-amine;
(7R,9aS)-trans-(2-Benzo[d]isoxazol-3-yl-octahydro-pyrido[1,2-a]pyrazin-7-ylmethyl)-(5-methyl-pyrimidin-2-yl)amine;
(7S,9aS)-cis-(2-Benzo[d]isoxazol-3-yl-octahydro-pyrido[1,2-a]pyrazin-7-ylmethyl)-(5-methyl-pyrimidin-2-yl)-amine;
(7R,9aS)-trans-(2-Benzo[d]isoxazol-3-yl-octahydro-pyrido[1,2-a]pyrazin-7-ylmethyl)-(5-chloro-pyrimidin-2-yl)-amine;
(7S,9aS )-cis-(2-Benzo[d]isoxazol-3-yl-octahydro-pyrido[1,2-a]pyrazin-7-ylmethyl)-(5-chloro-pyrimidin-2-yl)-amine;
(7R,9aS)-trans-(5-Chloro-pyrmidin-2-yl)-[2-(5-fluoro-benzo[d]isoxazol-3-yl)-octahydro-pyrido[1,2-a]pyrazin-7-ylmethyl]-amine;
(7S,9aS)-cis-(5-Chloro-pyrimidin-2-yl)-[2-(5-fluoro-benzo[d]isoxazol-3-yl)-octahydro-pyrido[1,2-a]pyrazin-7-ylmethyl]-amine;
(7R,9aS)-trans-[2-(5-Fluoro-benzo[d]isoxazol-3-yl)-octahydro-pyrido[1,2-a]pyrazin-7-ylmethyl]-(5-methyl-pyrimidin-2-yl)-amine;
(7S,9aS)-cis-[2-(5-Fluoro-benzo[d]isoxazol-3-yl)-octahydro-pyrido[1,2-a]pyrazin-7-ylmethyl]-(5-methyl-pyrimidin-2-yl)-amine;
(7R,9aS)-trans-(2-Benzo[d]isoxazol-3-yl-octahydro-pyrido[1,2-a]pyrazin-7-ylmethyl)-(5-fluoro-pyridin-2-yl)-amine;
(7S,9aS)-cis-(2-Benzo[d]isoxazol-3-yl-octahydro-pyrido[1,2-a]pyrazin-7-ylmethyl)-(5-fluoro-pyridin-2-yl)-amine;
(7R,9aS)-trans-[2-(5-Fluoro-benzo[d]isoxazol-3-yl)-octahydro-pyrido[1,2-a]pyrazin-7-ylmethyl]-(5-fluoro-pyridin-2-yl)-amine;
(7S,9aS)-cis-[2-(5-Fluoro-benzo[d]isoxazol-3-yl)-octahydro-pyrido[1,2-a]pyrazin-7-ylmethyl]-(5-fluoro-pyridin-2-yl)-amine;
(7R,9aS)-trans-(2-Benzo[d]isoxazol-3-yl-octahydro-pyrido[1,2-a]pyrazin-7-ylmethyl)-(5-fluoro-3-methyl-pyridin-2-yl)-amine;
(7S,9aS)-cis-(2-Benzo[d]isoxazol-3-yl-octahydro-pyrido[1,2-a]pyrazin-7-ylmethyl)-(5-fluoro-3-methyl-pyridin-2-yl)-amine;
(7R,9aS)-trans-[2-(5-Fluoro-benzo[d]isoxazol-3-yl)-octahydro-pyrido[1,2-a]pyrazin-7-ylmethyl]-pyridin-2-yl)-amine;
(7R,9aS)-trans-[2-(5-Fluoro-benzo[d]isoxazol-3-yloctahydro-pyrido[1,2-a]pyrazin-7-ylmethyl]-(5-fluoro-3-methyl-pyridin-2-yl)-amine;
(7S,9aS)-cis-[2-(5-Fluoro-benzo[d]isoxazol-3-yl)-octahydro-pyrido[1,2-a]pyrazin-7-ylmethyl]-(5-fluoro-3-methyl-pyridin-2-yl)-amine; and
(7R,9aS)-trans-(2-Benzo[d]isoxazol-3yl-octahydro-pyrido[1,2-a]pyrazin-7-yl-methyl(5-fluoro-pyrimidin-2-yl)-amine.

4. A pharmaceutical composition for treating a disorder or condition selected from hypertension, depression, generalized anxiety disorder, phobias, posttraumatic stress syndrome, avoidant personality disorder, premature ejaculation, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, cancer, chronic paroxysmal hemicrania and headache in a mammal, comprising an amount of a compound according to claim 1 that is effective in treating such disorder or condition and a pharmaceutically acceptable carrier.

5. A pharmaceutical composition for treating a disorder or condition that can be treated by modulating serotonergic neurotransmission in a mammal, comprising an amount of a compound according to claim 1 that is effective in treating such disorder or condition and a pharmaceutically acceptable carrier.

6. A pharmaceutical composition for treating a disorder or condition selected from hypertension, depression, generalized anxiety disorder, phobias, posttraumatic stress syndrome, avoidant personality disorder, premature ejaculation, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, cancer, chronic paroxysmal hemicrania and headache in a mammal, comprising a serotonin receptor antagonizing or agonizing effective amount of a compound according to claim 1 and a pharmaceutically acceptable carrier.

7. A pharmaceutical composition for treating a disorder or condition that can be treated by modulating serotonergic neurotransmission in a mammal, comprising a serotonin receptor antagonizing or agonizing effective amount of a compound of according to claim 1 and a pharmaceutically acceptable carrier.

8. A pharmaceutical composition for modulating serotonergic neurotransmission in a mammal, comprising:
   a) a pharmaceutically acceptable carrier;
   b) a compound of according to claim 1; and
   c) a 5-HT re-uptake inhibitor or a pharmaceutically acceptable salt thereof;
   wherein the amount of the active compounds are such that the combination is effective in treating such disorder or condition.

9. A pharmaceutical composition according to claim 8, wherein the 5-HT re-uptake inhibitor is sertraline or a pharmaceutically acceptable salt thereof.

10. A pharmaceutical composition for treating a disorder or condition that can be treated by modulating serotonergic neurotransmission in a mammal, comprising:
    a) a 5-HT1A agonist or antagonist or a pharmaceutically acceptable salt thereof; and
    b) a 5-HT1D antagonizing compound according to claim 1;
    wherein the amounts of the active compounds are such that the combination is effective in treating such disorder or condition.

11. A pharmaceutical composition for treating a disorder or condition selected from hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, cancer, chronic paroxysmal hemicrania and headache in a mammal, comprising:
    a) a 5-HT1A agonist or antagonist or a pharmaceutically acceptable salt thereof; and
    b) a 5-HT1D antagonizing compound according to claim 1;
    wherein the amounts of the active compounds are such that the combination is effective in treating such disorder or condition.

12. A method for treating a disorder or condition selected from hypertension, depression, generalized anxiety disorder, phobias, posttraumatic stress syndrome, avoidant personality disorder, premature ejaculation, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, cancer, chronic paroxysmal hemicrania and headache in a mammal, comprising administering to a mammal in need of such treatment an amount of a compound according to claim 1 that is effective in treating such disorder or condition.

13. A method for modulating serotonergic neurotransmission in a mammal, comprising administering to said mammal an effective amount of a compound according to claim 1.

14. A method for treating a disorder or condition selected from hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, cancer, chronic paroxysmal hemicrania and headache in a mammal, comprising administering to a mammal requiring such treatment a serotonin 1A receptor antagonizing or agonizing effective amount, or a serotonin 1D receptor antagonizing effective amount, of a compound according to claim 1.

15. A method for modulating serotonergic neurotransmission in a mammal, comprising administering to said mammal a serotonin 1A receptor antagonizing or agonizing effective amount, or a serotonin 1D receptor antagonizing effective amount, of a compound according to claim 1.

16. A method for modulating serotonergic neurotransmission in a mammal, comprising administering to said mammal:
    a) a compound according to claim 1; and
    b) a 5-HT re-uptake inhibitor or a pharmaceutically acceptable salt thereof;
    wherein the amounts of the active compounds are such that the combination is effective in said modulation.

17. A method according to claim 16, wherein the 5-HT re-uptake inhibitor is sertraline or a pharmaceutically acceptable salt thereof.

18. A method for treating a disorder or condition selected from hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, cancer, chronic paroxysmal hemicrania and headache in a mammal, comprising administering to a mammal requiring such treatment:
    a) a compound according to claim 1; and
    b) a 5HT re-uptake inhibitor or a pharmaceutically acceptable salt thereof;
    wherein the amounts of the active compounds are such that the combination is effective in treating such disorder or condition.

19. A method for modulating serotonergic neurotransmission in a mammal, comprising administering to said mammal:
 a) a 5-HT1A antagonist or agonist or a pharmaceutically acceptable salt thereof; and
 b) a 5-HT1D antagonizing compound according to claim 1;
 wherein the amounts of the active compounds are such that the combination is effective in treating such disorder or condition.

20. A method for treating a disorder or condition selected from hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, male impotence, cancer, chronic paroxysmal hemicrania and headache in a mammal, comprising administering to a mammal requiring such treatment:
 a) a 5-HT1A agonist or antagonist or a pharmaceutically acceptable salt thereof; and
 b) a 5-HT1D antagonizing compound according to claim 1;
 wherein the amounts of the active compounds are such that the combination is effective in said treatment.

* * * * *